(12) United States Patent
Chen et al.

(10) Patent No.: US 6,270,805 B1
(45) Date of Patent: *Aug. 7, 2001

(54) TWO PELLET CONTROLLED RELEASE FORMULATION FOR WATER SOLUBLE DRUGS WHICH CONTAINS AN ALKALINE METAL STEARATE

(75) Inventors: Chih-Ming Chen; Xiu Xiu Cheng, both of Davie, FL (US)

(73) Assignee: Andrx Pharmaceuticals, Inc., Davie, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/187,319

(22) Filed: Nov. 6, 1998

(51) Int. Cl.⁷ .............................. A61K 9/16; A61K 47/00
(52) U.S. Cl. ..................... 424/497; 424/490; 424/494; 514/785; 514/786; 514/970
(58) Field of Search ..................... 424/490, 494, 424/470, 471, 497, 480; 514/785, 786, 970

(56) References Cited

U.S. PATENT DOCUMENTS

| | | |
|---|---|---|
| 4,894,240 | 1/1990 | Geoghegan et al. . |
| 5,133,974 * | 7/1992 | Paradissis et al. . |
| 5,137,733 | 8/1992 | Noda et al. . |
| 5,229,135 * | 7/1993 | Philippon et al. . |
| 5,252,337 * | 10/1993 | Powell . |
| 5,260,068 | 11/1993 | Chen . |
| 5,439,689 | 8/1995 | Hendrickson et al. . |
| 5,445,829 * | 8/1995 | Paradissis et al. . |
| 5,529,791 * | 6/1996 | Deboeck et al. . |
| 5,567,441 * | 10/1996 | Chen . |
| 5,830,503 * | 11/1998 | Chen . |
| 5,834,023 * | 11/1998 | Chen . |
| 5,840,329 * | 11/1998 | Bai . |
| 6,033,687 | 3/2000 | Heinicke et al. . |

* cited by examiner

Primary Examiner—Thurman K. Page
Assistant Examiner—Brian K. Seidleck
(74) Attorney, Agent, or Firm—Hedman & Costigan, P.C.

(57) ABSTRACT

A once-a-day controlled release formulation of a water soluble drug is described which includes:

(a) from 20 to 50% by weight of enteric polymeric membrane coated pellets comprising a polymer membrane coated core which comprises a biologically inert core which is coated with a first layer which consists essentially of a water soluble drug and a binder; and a second layer which comprises a membrane comprising a pH dependent polymeric material; and (b) from 50% to 80% by weight of delayed pulse polymeric membrane coated pellets comprising a polymeric membrane coated core which comprises a biologically inert core which is coated with a first layer which consists essentially of a water soluble drug and a binder and a second layer which comprises a polymeric membrane and a alkaline earth metal stearate which will substantially maintain its integrity in the varying pH conditions of the gastrointestinal tract but is permeable to said water soluble drug; and (c) a unit dose containment system.

18 Claims, 4 Drawing Sheets

TWO PELLET CONTROLLED RELEASE FORMULATION FOR WATER SOLUBLE DRUGS WHICH CONTAINS AN ALKALINE METAL STEARATE

BACKGROUND OF THE INVENTION

The present invention relates to controlled release unit dose formulations of water soluble drugs in general which are exemplified by diltiazem hydrochloride (diltiazem). There is a need for a means for varying the release rates of water soluble drugs from multiparticulate beads which have release membranes that are applied by a coating process. Diltiazem is sold commercially in extended release pharmaceutical dosage forms in order to maintain a therapeutic serum level of diltiazem and to minimize the effects of missed doses of drugs caused by a lack of patient compliance. The minimum therapeutic plasma diltiazem concentrations are in the range of 50 to 200 ng/ml.

Cardizem® CD is described as a once-a-day extended release capsule containing diltiazem and fumaric acid. In the file history of U.S. Pat. No. 5,286,497, representations were made that the formulation disclosed in that patent is the formulation for Cardizem® CD. The formulation for Cardizem® CD is identified in the file history of U.S. Pat. No. 5,286,497 as having a "stair-step release profile" which has a rapid release bead and an extended release bead.

U.S. Pat. No. 5,567,441 also discloses a formulation of diltiazem which is bioequivalent to Cardizem® CD but has a different release profile in hydrochloric acid. That formulation exhibits a slower in vitro release profile in 0.1N hydrochloric acid than the slow release bead of the present invention but exhibits substantially the same in vivo release profile.

In U.S. Pat. No. 5,229,135 and in U.S. Pat. No. 5,529,791, once-a-day formulations are described that are based on a single pellet which is prepared with an active core which is coated with diltiazem and an inner and outer membrane. Other diltiazem formulations are disclosed in U.S. Pat. No. 4,721,619; U.S. Pat. No. 4,894,240; U.S. Pat. No. 5,002,776; U.S. Pat. Nos. 5,364,620; 4,891,230; U.S. Pat. No. 4,917,899; U.S. Pat. No. 5,288,505; and U.S. Pat. No. 5,336,504.

The present invention provides novel water soluble pharmaceutical formulations which are two-pellet based capsule formulations. The diltiazem formulations made according to the present invention do not have a "stair-step release profile" but do provide a "two- peak pharmacokinetic profile". Moreover, the diltiazem formulations of the present invention does not require the presence of fumaric acid or any other organic acid in the core. The present invention also provides a means for varying the release rates of water soluble to allow for faster in vitro release of the drug.

SUMMARY OF THE INVENTION

The present invention is directed to a once-a-day controlled release water soluble pharmaceutical formulation which comprises:

(a) from 20 to 50% by weight of polymeric enteric coated pellets comprising a polymer membrane coated core which comprises a biologically inert core which is coated with a first layer which consists essentially of a water soluble drug and a polymeric binder; and a second layer which comprises a membrane comprising a polymeric enteric coating material; and (b) from 50% to 80% by weight of delayed pulse polymeric membrane coated pellets comprising a polymeric membrane coated core which comprises a biologically inert core which is coated with a combined first layer which consists essentially of a water soluble drug and a polymeric binder and a second layer which comprises a polymeric membrane and an alkaline earth metal stearate said second layer being capable of substantially maintaining its integrity in the varying pH conditions of the gastrointestinal tract and being permeable to said water soluble drug; and (c) a unit dose containment system.

The present invention also provides a dosage form of diltiazem which exhibits in 0.1N HCl, a release rate profile which is initially a relatively slow, zero order release rate that continues for up to about 12–14 hours. Thereafter, there is a sharp increase in the rate of release which can be characterized as a delayed pulse.

It is surprising and unexpected that the combined zero order-delayed pulse in vitro release characteristics of the diltiazem dosage form of the present invention provides substantially the same in vivo "two peak" plasma levels of diltiazem which is provided by a commercial formulation which exhibits in vitro a stair-step type of release profile.

It is an object of the invention to provide a once-a-day water soluble drug dosage system.

It is also an object of the present invention to provide a once-a-day water soluble drug dosage system which is free of any organic acid component.

It is also an object of this invention to provide an organic acid free, once-a-day diltiazem dosage system which is therapeutically or biologically equivalent to a once-a-day stair step diltiazem dosage system which contains an organic acid.

It is also an object of this invention to provide a once a day diltiazem dosage system which is bioequivalent to Cardizem® CD but has a different in vitro release profile when the release profile is determined in 0.1N hydrochloric acid.

These and other objects of the invention will become apparent from the appended specification.

DETAILED DESCRIPTION OF THE INVENTION

Figure 1:
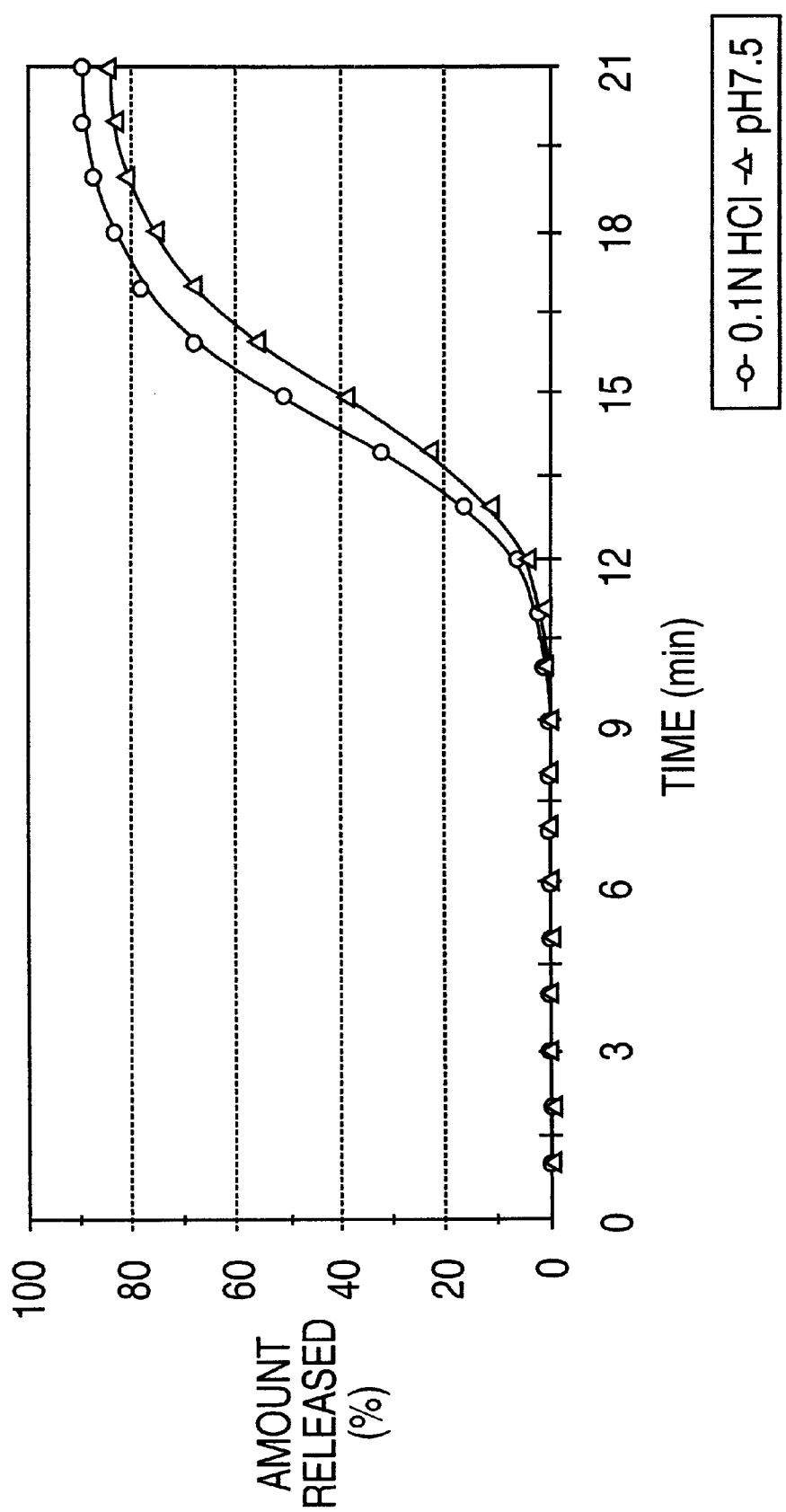
FIG. 1 is a graph which shows the in vitro dissolution rate of diltiazem delayed pulse membrane coated core pellets prepared according to Example 1 of the present invention in 0.1N HCl using a USP Type II apparatus at 37° C. and 100 rpm and simulated intestinal fluid (pH 7.5) using a USP Type II apparatus at 37° C. and 75 rpm

The once-a-day, controlled release formulation for water soluble drugs provides an alternative to prior art formulations for once-a-day dosing of drugs that are to be maintained at a steady state level in the blood plasma.

Suitable water soluble drugs which are useful in the dosage formulation of the present invention include diltiazem hydrochloride, verapamil hydrochloride, bupropion hydrochloride, metformin hydrochloride, propranolol hydrochloride, dextromethorphan hydrobromide, diphenhydramine hydrochloride, disopyramide hydrochloride, tramadol, fluoxetine hydrochloride, paroxetine hydrochloride, pentoxifylline hydrochloride and the like.

Both the enteric polymer membrane coated pellet and the delayed pulse polymer membrane coated pellet are based on an active core which contains the diltiazem hydrochloride. The core is made by coating a biologically inactive core component such as non-pareil sugar particles i.e., sugar spheres NF, starch granules, clay particles or other material on which may be deposited a coating of diltiazem hydrochloride in combination with a polymeric binder which comprises from 5 to 10 wt % (based on the combined weight of the binder and the diltiazem). The binder can be any pharmaceutically acceptable binding agent known to the art such as ethylcellulose, polyvinylpyrrolidone, hydroxypropyl methylcellulose and hydroxypropylcellulose. The binder is applied using conventional solvents which are removed from the product during processing.

The active core component is provided with an enteric coating which is a polymeric enteric coating material to form a rapid release bead. The enteric coatings are "pH dependent" which describes the well known effect of an enteric coating which prevents release of the dosage form in the low pH conditions of the stomach but permits release in the higher pH conditions of the small intestine. The enteric coating will comprise from 4 to 15% preferably from 5 to 11% by weight based on the combined weight of the active core component and the total weight of the coating. The enteric coating polymer may be selected from the group consisting of shellac, methacrylic acid copolymers, (Eudragit S or L) cellulose acetate phthalate, hydroxypropylmethylcellulose phthalate, hydroxypropylmethylcellulose acetate succinate, cellulose acetate trimellitate and polyvinyl acetate phthalate. Methacrylic acid copolymer, Type B USP/NFXXII which dissolves at a pH above about 7.0 is preferred. The thickness of the coating is selected to provide the desired release rate depending on the thickness of the coating and the particular coating.

A commercially available copolymer is Eudragit S100 which is based on methacrylic acid and methyl methacrylate and has a weight average molecular weight of about 150,000. Other auxiliary coating aids such as a minor amount (1–5 wt % based on the active core component and the total weight of the final coating) of a plasticizer such as acetyltributyl citrate, triacetin, acetylated monoglyceride, rape oil, olive oil, sesame oil, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, polyethyleneglycol (molecular weight of from 380 to 420), propylene glycol and mixtures thereof in combination with an antisticking agent which is selected from the group consisting of an alkaline earth metal stearate, such as magnesium stearate or calcium stearate, or talc. The antisticking agents can be used alone or in combination. The antisticking agent may be added in an amount which is equivalent to 0.3 to 1.0:1.0 by weight of the methacrylic acid copolymer. These amounts may be varied to obtain the particular release rate that is desired. These components may be added to the methacrylic acid copolymer in combination with appropriate solvents.

The delayed pulse polymeric coated pellet contains an active core which is coated with a polymeric material which will substantially maintain its integrity in the varying pH conditions of the gastrointestinal tract but is permeable to diltiazem. The delayed pulse polymeric pellet is designed to release not less than 65% and preferably not less than 75% of diltiazem in vitro about 18 hours after the dosage form of the invention is placed in 0.1N HCl. The rate of release for the delayed pulse pellet is sharply increased, i.e. about 3 to 5 times, as compared to the in vitro rate of release of the enteric coated diltiazem pellets of the invention.

The delayed pulse pellets are made by coating the active core component with 15 is 35 wt % and preferably from 15 to 30 wt % (based on the combined weight of the active core and the total weight of the final coating) of a polymer such as ethyl cellulose, cellulose acetate, cellulose acetate butyrate, or an acrylic copolymer which when used in a sufficient amount will cause the delayed pulse pellet to begin to release diltiazem 10 to 12 hours after the ingestion of the dosage form of the invention. Materials such as Eudragit RS 30D; RS 100; NE 30D; RL 30D or RL 100 may be used to prepare the delayed pulse pellet. A preferred material is an acrylate copolymer which has a permeability which is independent of pH. Such a preferred acrylate copolymer is commercially available as Eudragit RS30D which is available as a 30 wt % aqueous dispersion of copolymers of acrylic and methacrylic acid esters, having a number average molecular weight of 150,000 with a low content of quaternary ammonium groups. Other auxiliary coating aids such as a minor amount (2–7 wt % based on the active core component and the total weight of the final coating) of a plasticizer such as acetyltributyl citrate, triacetin, acetylated monoglyceride, rape oil, olive oil, sesame oil, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, polyethyleneglycol (molecular weight of from 380 to 420), propylene glycol and mixtures thereof in combination with an antisticking agent which comprises a alkaline earth stearate such as magnesium or calcium stearate alone or in combination with talc in an amount which is equivalent to 0.3 to 0.75:1 by weight of the acrylate copolymer, may be added to the acrylate copolymer in combination with appropriate solvents.

The controlled release diltiazem formulation of the invention will preferably have a dissolution release rate in simulated intestinal fluid (pH7.5) in a USP XXII Type II apparatus at 37° C. and 75 rpm which substantially corresponds to the following:
  a) from 20 to 50 wt % and preferably from 25 to 45 wt % of total diltiazem is released after 2 hours;
  b) from 30 to 65 wt % and preferably from 35 to 55 wt % of total diltiazem is released after 12 hours;
  c) from 60 to 95 wt % and preferably from 65 to 90 wt % of total diltiazem is released after 18 hours;
  d) not less than 75 wt % and preferably not less than 80 wt % of total diltiazem is released after 24 hours.

The enteric coated diltiazem beads of the invention will preferably have a dissolution release rate in hydrochloric acid, 0.1N in a USP XXII Type II apparatus at 37° C. and 100 rpm which substantially corresponds to the following:
  a) from 0 to 20 wt % and preferably from 0 to 10 wt % of total diltiazem is released after 3 hours;
  b) from 0 to 25 wt % and preferably from 0–20 wt % of total diltiazem is released after 6 hours.

The delayed pulse diltiazem beads of the invention will preferably have a dissolution release rate in hydrochloric acid, 0.1N, in a USP XXII Type II apparatus at 37° C. and 100 rpm which substantially corresponds to the following:

a) from 0 to 15 wt % and preferably not more than 10 % of total diltiazem is released after 12 hours;

b) from 65 to 90 wt % of total diltiazem and preferably 70 to 85 wt % is released after 18 hours;

c) not less than 80 wt % of total diltiazem is released after 24 hours.

The enteric polymer pellets of the invention and the delayed pulse polymer membrane coated pellets may be placed in soft or hard gelatin capsules or in other dosage forms such as tablets which contain a cushioning agent to prevent damage to the pellets or the polyethylene glycol based dosage formulation which is disclosed in U.S. Pat. No. 5,458,888, which is incorporated by reference.

Generally the dosage form will contain from about 20 to 50 wt % and preferably about 40 wt % of the enteric polymer membrane coated pellets and from about 50 to 80 wt % and preferably about 60 wt % of the delayed pulse polymer coated pellets.

DESCRIPTION OF THE PREFERRED EMBODIMENTS

EXAMPLE 1

A diltiazem hydrochloride active pellet (A) having the following formulation was prepared:

| | | |
|---|---|---|
| diltiazem hydrochloride, USP | 70.0 wt % | 168.0 kg |
| sugar spheres, NF (30/35) | 23.67 wt % | 56.8 kg |
| ethylcellulose, NF (Ethocel 10 cps) | 5.83 wt % | 14.0 kg |
| polysorbate 80 NF | 0.5 wt % | 1.20 kg |
| isopropyl alcohol, USP* | * | 325.7 kg |
| | 100.0 | 240.00 kg |

*evaporated during processing

Add the ethylcellulose in the isopropyl alcohol in a stainless steel tank. The diltiazem hydrochloride (micronized) is added to the ethylcellulose solution with continued agitation for at least 10 minutes with the homogenizer under conditions that avoid the formation of lumps or the introduction of air which will cause foaming. The polysorbate 80 is then added while mixing with a homogenizer. The coating suspension is sprayed onto the sugar spheres in a fluidized bed coater under the following conditions: product temp. 20–35° C.; atomization pressure 2–4 bars; air volume 700–1800 m³/L and a pump rate of 300–1500 mg/min. After spraying, the pellets are dried in the fluidized bed coater for approximately 10 minutes and then cooled and collected using a particle size separator.

The diltiazem active pellets (A) are then coated with the enteric polymer to form enteric polymer membrane coated diltiazem rapid release pellets as follows:

| | | |
|---|---|---|
| diltiazem HCl Active pellets (A) | 93.0 wt % | 98.58 kg |
| methacrylic acid copolymer (Eudragit S100) | 4.725 wt % | 5.01 kg |
| acetyltributyl citrate | 0.70 wt % | 0.74 kg |
| talc, USP | 1.575 wt % | 1.67 kg |
| isopropyl alcohol, USP | | 111.0 kg |
| purified water, USP | | 3.14 kg |
| | 100.0 wt % | 106.0 kg |

The acetyl tributyl citrate is dissolved in the isopropyl alcohol in a stainless steel tank while homogenizing. The Eudragit S-100 is added to the acetyltributyl citrate/isopropyl alcohol solution until it completely dissolves. Purified water is added to the polymer solution to provide a clear solution. Then the talc is dispersed in the solution while mixing until a uniform coating suspension is formed. The solution is continuously stirred throughout the coating process to prevent sedimentation of the talc.

Extended release or delayed pulse diltiazem pellets (SR2) are prepared using the following coating suspension:

| | | |
|---|---|---|
| diltiazem HCl active pellets (A) | 71.86 wt % | 107.55 kg |
| acrylic acid copolymer (Eudragit RS30D) | 16.406 wt % | 82.68 kg |
| acetyltributyl citrate | 3.327 wt % | 4.98 kg |
| magnesium stearate | 0.250 wt % | 0.375 kg |
| talc, USP | 8.065 wt % | 12.07 kg |
| polysorbate 80 | 0.092 wt % | 0.138 kg |
| purified water, USP* | | 111.73 kg |
| | 100.0 wt % | |
| talc (for dusting after coating) | | 3.00 kg |

*evaporates during processing

Processing Procedures:

1. Add the polysorbate 80 to the purified water while homgenizing for 10 minutes.
2. Add the magnesium stearate to the solution of the polysorbate 80 and homogenized for 5 minutes.
3. Add the acetyltributyl citrate to the solution above while homogenizing for 3 minutes.
4. Add talc to the dispersion above and mix for 10 minutes.
5. Add the dispersion prepared above into the acrylic polymer dispersion and mix for at least 10 minutes before spray coating the active pellets. Keep stirring during the coating process. The diltiazem active pellets are loaded into a fluidized bed coater at an inlet temperature of 50° C. The pellets are preheated at a temperature of 50° C. for 3 minutes.

The following conditions are used during spray coating: product temperature: first hour; 35–40° C. thereafter 32–35° C. atomization pressure; 3–4 bar; pump rate; first hour: 300–600 g/min, then 600–1500g/min. After all coating suspension is consumed, dry the pellets in the fluidized bed for 5 minutes. Then cool the pellets until the product temperature drops to 25–30° C. and discharge the coated pellets while dusting with talc. The pellets are then dried in an oven at 60° C. for at least 40 hours. The resultant pellets are mixed with the rapid release beads in a ratio of 4:6 based on the content of diltiazem HCl. Then, the blended pellets are encapsulated into a hard gelatin capsule to manufacture the diltiazem HCl ER capsules 300 mg.

EXAMPLE 2

This Example provides an alterative delayed pulse bead formula which is made using the procedure of Example 1:

| | | |
|---|---|---|
| diltiazem HCl active pellets | 69.30 wt % | 120 g |
| acrylic acid copolymer (Eudragit RS30D) | 18.0 wt % | 103.89 g |
| talc | 8.0 wt % | 13.85 g |
| magnesium stearate | 1.0 wt % | 1.73 g |
| acetyltributyl citrate | 3.6 wt % | 6.24 g |
| polysorbate 80 | 0.1 wt % | 0.18 kg |

COMPARATIVE EXAMPLE 3

This Example provides an alternative delayed pulse bead formula which is made using the procedure of Example 1 without magnesium stearate:

| | | |
|---|---|---|
| diltiazem HCl Active pellets | 69.30 wt % | 120 g |
| acrylic acid copolymer (Eudragit RS30D) | 18.0 wt % | 103.89 g |
| talc | 9.0 wt % | 13.85 g |
| acetyltributyl citrate | 3.6 wt % | 6.24 g |
| polysorbate 80 | 0.1 wt % | 0.18 kg |

Where reference is made to a USP Type II apparatus, that apparatus is intended to be the USP dissolution apparatus described in USP XXII which is incorporated by reference.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

What is claimed is:

1. A once-a-day controlled release formulation of a water soluble drug which comprises:
   (a) from 20 to 50% by weight of enteric polymeric membrane coated pellets comprising a polymer membrane coated core which comprises a biologically inert core which is coated with a first layer which consists essentially of a water soluble drug and a binder; and a second layer which comprises a membrane comprising an enteric coating material; and
   (b) from 50% to 80% by weight of delayed release polymeric membrane coated pellets comprising a polymeric membrane coated core which comprises a biologically inert core which is coated with a first layer which consists essentially of a water soluble drug and a binder polymer and a second layer which comprises a polymeric membrane, talc and an alkaline earth metal stearate said second layer being capable of substantially maintaining its integrity in the varying pH conditions of the gastrointestinal tract and being permeable to said water soluble drug; and
   (c) a unit dose containment system.

2. A once-a-day controlled release formulation of a water soluble drug as defined in claim 1 which comprises about 40 wt % of (a) and about 60 wt % of the pellets of (b).

3. A once-a-day controlled release formulation of a water soluble drug as defined in claim 1 wherein the enteric polymeric coating material is selected from the group consisting of shellac, methacrylic acid copolymers, hydroxypropyl methylcellulose phthalate and cellulose acetate phthalate.

4. A once-a-day controlled release formulation of a water soluble drug as defined in claim 1 wherein the enteric polymeric coating material and the second layer on the delayed pulse pellets both contain a plasticizer.

5. A once-a-day controlled release formulation of a water soluble drug as defined in claim 4 wherein the plasticizer is acetyltributyl citrate.

6. A once-a-day controlled release formulation of a water soluble drug as defined in claim 3 wherein the membrane on the enteric coating polymeric material is a methacrylic acid copolymer.

7. A once-a-day controlled release formulation of a water soluble drug as defined in claim 1 wherein the second layer on the delayed pulse polymeric membrane coated pellets comprises a copolymer of acrylic and methacrylic acid esters with a low content of ammonium groups, magnesium stearate and talc.

8. A once-a-day controlled release of a formulation of a water soluble drug as defined in claim 1 which exhibits in 0.1N HCl, a release rate profile which is initially a zero order release rate of the water soluble drug that continues for up to about 12–14 hours and thereafter exhibits a sharp increase in the rate of release of said water soluble drug.

9. A delayed pulse bead formulation of a water soluble drug which comprises membrane coated pellets comprising a polymeric membrane coated core which comprises a biologically inert core which is coated with a first layer which consists essentially of a water soluble drug and a polymeric binder polymer and a second layer which comprises a polymeric membrane, an alkaline earth metal stearate and talc said second layer being capable of substantially maintaining its integrity in the varying pH conditions of the gastrointestinal tract and being permeable to said water soluble drug and which resists any substantial release of said water soluble drug for 12 hours in a USP dissolution Type II apparatus at 37° C., 100 rpm in hydrochloric acid at pH 1.0.

10. A once-a-day controlled release formulation of diltiazem which comprises:
    (a) from 20 to 50% by weight of enteric polymeric membrane coated pellets comprising a polymer membrane coated core which comprises a biologically inert core which is coated with a first layer which consists essentially of a water soluble drug and a binder; and a second layer which comprises a membrane comprising an enteric coating material; and
    (b) from 50% to 80% by weight of delayed release polymeric membrane coated pellets comprising a polymeric membrane coated core which comprises a biologically inert core which is coated with a first layer which consists essentially of a water soluble drug and a binder polymer and a second layer which comprises a polymeric membrane, talc and an alkaline earth metal stearate said second layer being capable of substantially maintaining its integrity in the varying pH conditions of the gastrointestinal tract and being permeable to diltiazem; and
    (c) a unit dose containment system.

11. A once-a-day controlled release diltiazem formulation as defined in claim 10 which comprises about 40 wt % of (a) and about 60 wt % of the pellets of (b).

12. A once-a-day controlled release diltiazem formulation as defined in claim 10 wherein the enteric coating polymeric material is selected from the group consisting of shellac, methacrylic acid copolymers, hydroxy propylmethylcellulose phthalate and cellulose acetate phthalate.

13. A once-a-day controlled release diltiazem formulation as defined in claim 10 wherein the enteric coating polymeric material and the second layer on the delayed pulse pellets both contain a plasticizer.

14. A once-a-day controlled release diltiazem formulation as defined in claim 13 wherein the plasticizer is acetyltributyl citrate.

15. A once-a-day controlled release diltiazem formulation as defined in claim 12 wherein the membrane on the enteric coating polymeric material is a methacrylic acid copolymer.

16. A once-a-day controlled release diltiazem formulation as defined in claim 10 wherein the second layer on the delayed pulse polymeric membrane coated pellets comprises a copolymer of acrylic and methacrylic acid esters with a low content of ammonium groups, magnesium stearate and talc.

17. A once-a-day controlled release diltiazem formulation as defined in claim 10 which exhibits in 0.1N HCl, a release rate profile which is initially a zero order release rate of diltiazem that continues for up to about 12–14 hours and thereafter exhibits a sharp increase in the rate of release of diltiazem.

18. A delayed pulse diltiazem bead formulation which comprises membrane coated pellets comprising a polymeric membrane coated core which comprises a biologically inert core which is coated with a first layer which consists essentially of diltiazem and a polymeric binder polymer and a second layer which comprises a polymeric membrane, an alkaline earth metal stearate and talc, said second layer being capable of substantially maintaining its integrity in the varying pH conditions of the gastrointestinal tract and being permeable to diltiazem and which resists any substantial release of diltiazem for 12 hours in a USP dissolution Type II apparatus at 37° C., 100 rpm in hydrochloric acid at pH 1.0.

* * * * *

UNITED STATES PATENT AND TRADEMARK OFFICE
CERTIFICATE OF CORRECTION

Figure 2:
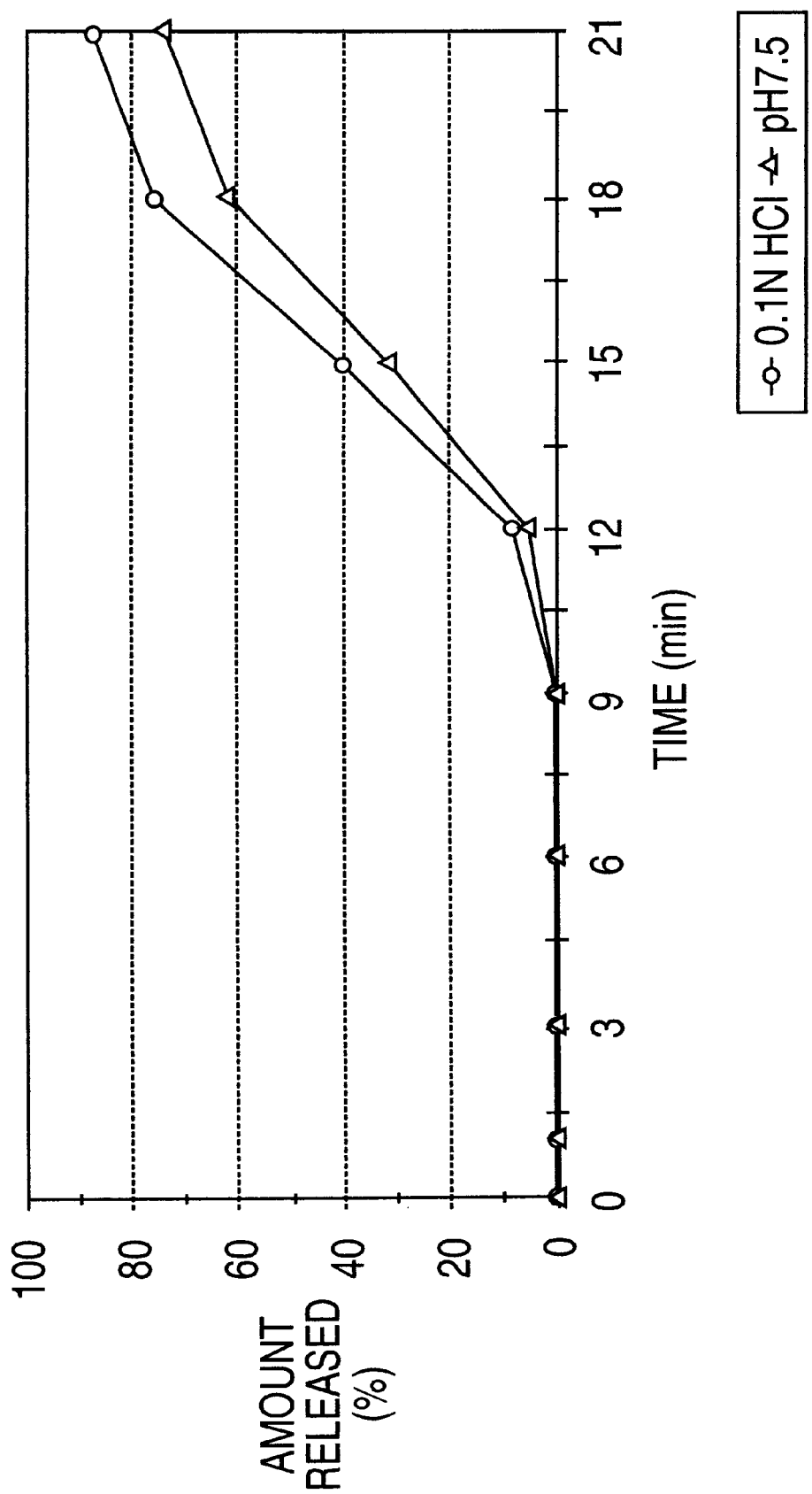
FIG. 2 is a graph which shows the in vitro dissolution rate of diltiazem delayed pulse membrane coated core pellets prepared according to Example 2 of the present invention in 0.1N HCl and simulated intestinal fluid (pH 7.5) using a USP Type II apparatus at 37° C. and 100 rpm.
Figure 3:
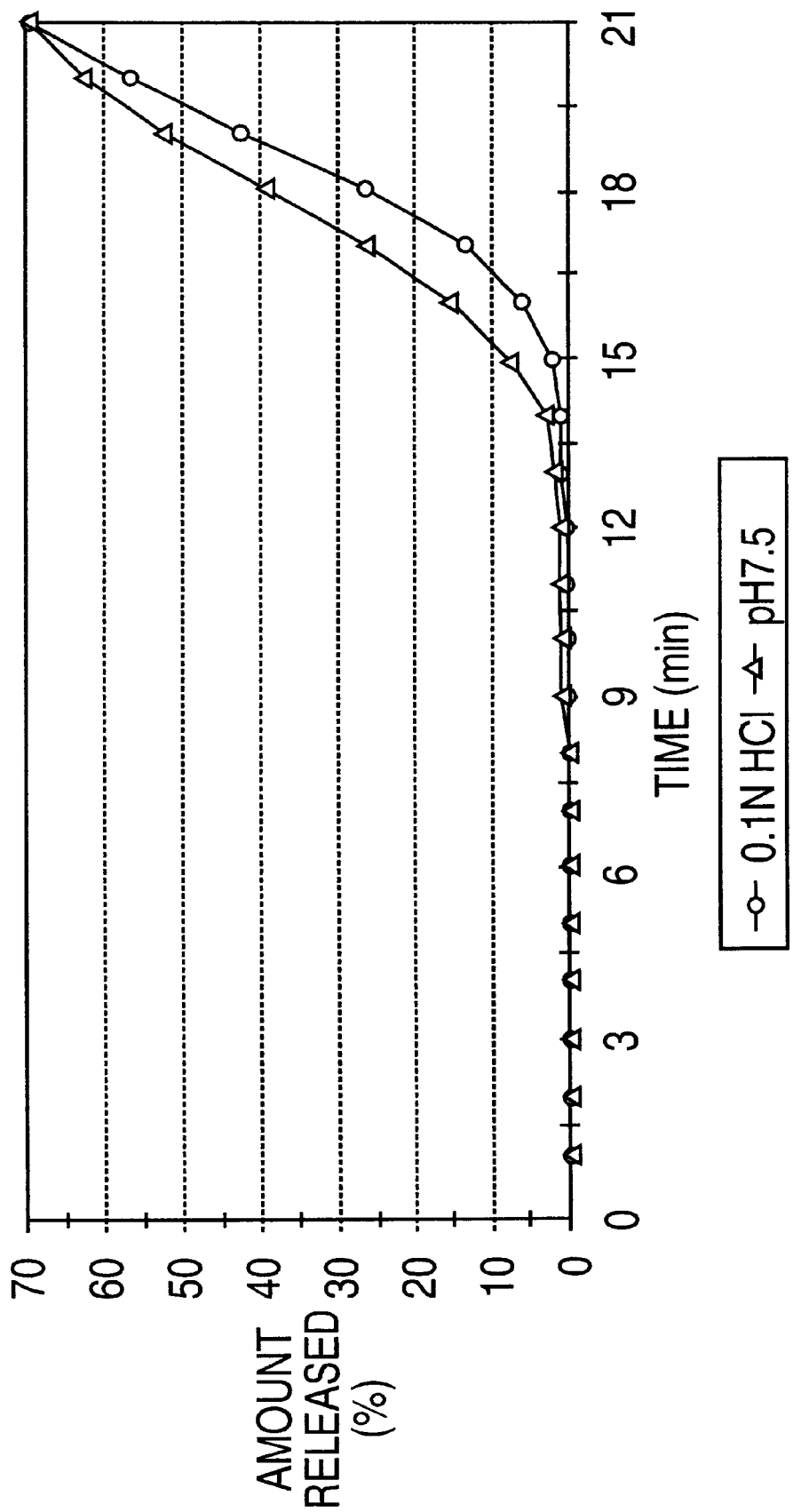
FIG. 3 is a graph which shows the in vitro dissolution rate of diltiazem delayed pulse membrane coated core pellets prepared according to Comparative Example 3 of the present application in 0.1N HCl and simulated intestinal fluid (pH 7.5) using a USP Type II apparatus at 37° C. and 100 rpm.
Figure 4:
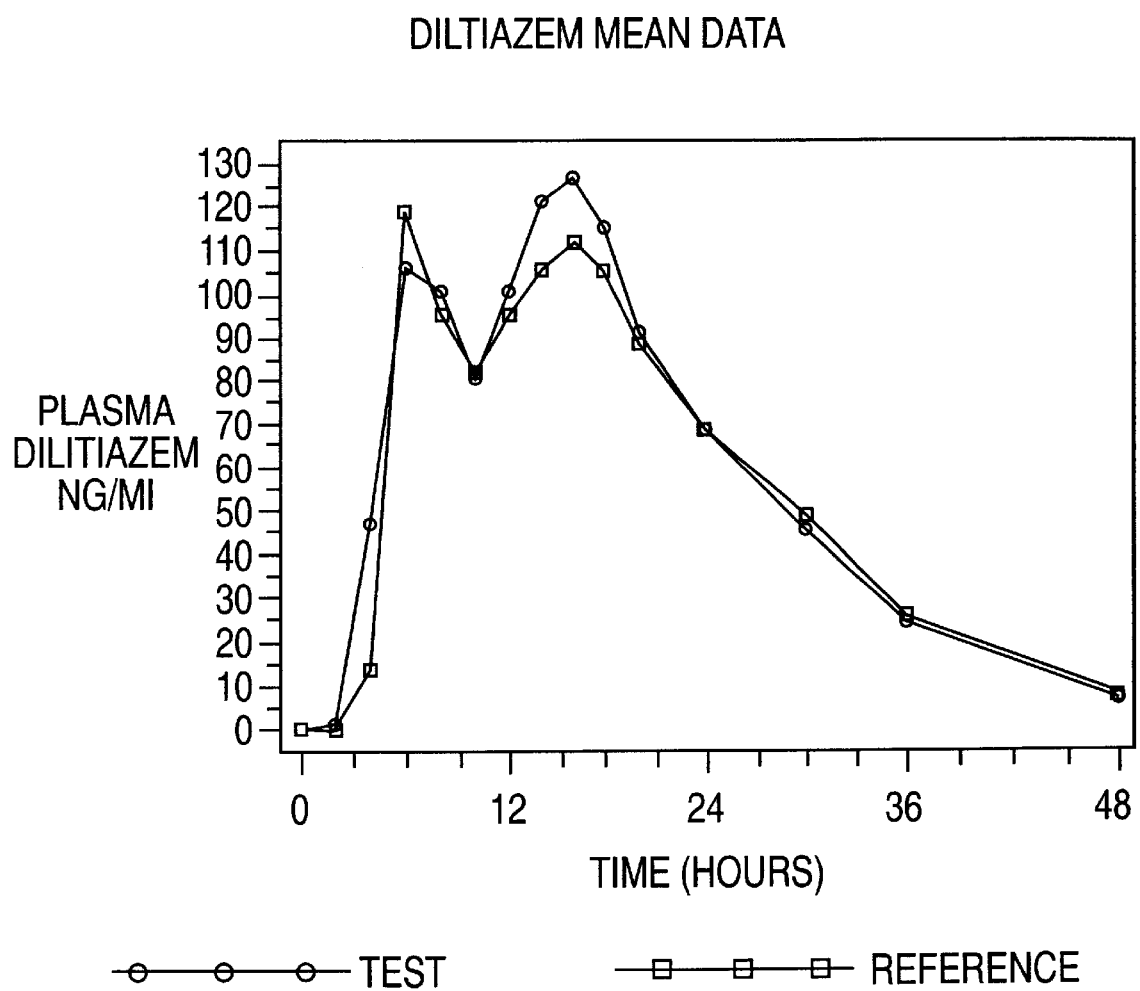
FIG. 4 is a graph which shows a plot of the mean plasma diltiazem concentrations versus time, of a diltiazem formulation prepared according to Example 1 with the points shown by circles and a plot of the mean diltiazem concentrations of Cardizem® CD where the reference points are shown by squares.

PATENT NO.   : 6,270,805 B1
DATED        : August 7, 2001
INVENTOR(S)  : Chih-Ming Chen and Xiu Xiu Cheng It is certified that error appears in the above-identified patent and that said Letters Patent is hereby corrected as shown below:

<u>Drawings,</u>
Figs. 1-3, should read -- Time(hours) -- not "Time(min)".

Signed and Sealed this

Eleventh Day of May, 2004

JON W. DUDAS
*Acting Director of the United States Patent and Trademark Office*